United States Patent [19]

Meyers et al.

[11] Patent Number: 4,802,466
[45] Date of Patent: Feb. 7, 1989

[54] LIGHTWEIGHT, COMPACT ORTHOTIC DEVICE FOR CONTROLLING KNEE INSTABILITIES

[75] Inventors: Andrew H. Meyers, 31 The Birches, Roslyn Estates, N.Y. 11576; Jeffrey Minkoff, New York, N.Y.

[73] Assignee: Andrew H. Meyers, Roslyn Estates, N.Y.

[21] Appl. No.: 38,048

[22] Filed: Apr. 14, 1987

[51] Int. Cl.⁴ .............................................. A61F 5/04
[52] U.S. Cl. ..................................... 128/80 C; 128/88
[58] Field of Search ..................... 128/80 C, 80 R, 83, 128/87 R, 88, 89 R, 84 R, 99, 100; 2/22, 24; 623/32

[56] References Cited

U.S. PATENT DOCUMENTS

| | | | |
|---|---|---|---|
| 2,235,142 | 3/1941 | Dye | 623/32 |
| 3,581,741 | 6/1981 | Rosman et al. | |
| 4,275,716 | 6/1981 | Scott, Jr. | 128/80 C |
| 4,372,298 | 2/1983 | Lerman | |
| 4,503,846 | 3/1985 | Martin | |
| 4,506,661 | 3/1985 | Foster | 128/80 C |
| 4,565,190 | 1/1986 | Pirmantgen et al. | 128/80 C |
| 4,624,247 | 11/1986 | Ford | 128/80 C |
| 4,632,097 | 12/1986 | Brooks | 128/80 C |
| 4,632,098 | 12/1986 | Grundel et al. | 128/80 C |
| 4,643,176 | 2/1987 | Mason et al. | 128/80 C |
| 4,681,097 | 7/1987 | Pansiera | 128/88 |

FOREIGN PATENT DOCUMENTS 246330  4/1966  Austria ................................. 623/32

OTHER PUBLICATIONS

"The Lenox Hill Derotation Brace", Lenox Hill Brace Shop, Inc.

Primary Examiner—Robert A. Hafer
Assistant Examiner—Kevin G. Rooney
Attorney, Agent, or Firm—Sixbey, Friedman, Leedom & Ferguson

[57] ABSTRACT

An orthotic device for controlling knee instabilities is disclosed herein that comprises a joint structure, upper and lower support assemblies including C-shaped bands for supporting the joint structure over the knee, an L-shaped condyle pad assembly having an upper portion for supporting the inner condyle region of the knee and an anterior extension for supporting the upper tibia against tibial displacements, and a mounting means including a V-shaped resilient strap for maintaining the upper portion of the condyle pad assembly in intimate supporting contact with the condyle region throughout the entire range of pivotal movement of the knee.

14 Claims, 2 Drawing Sheets

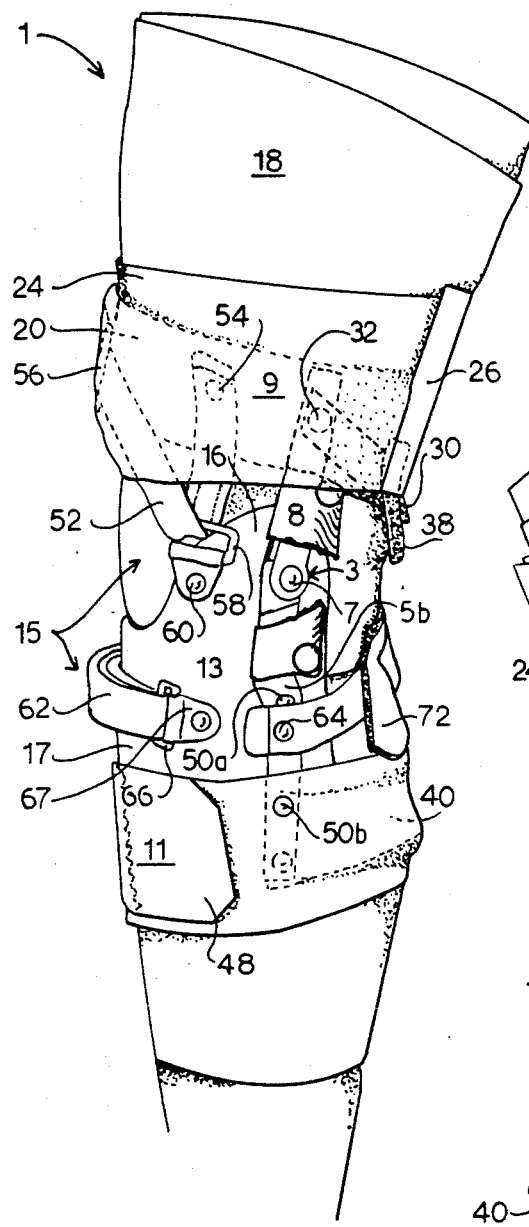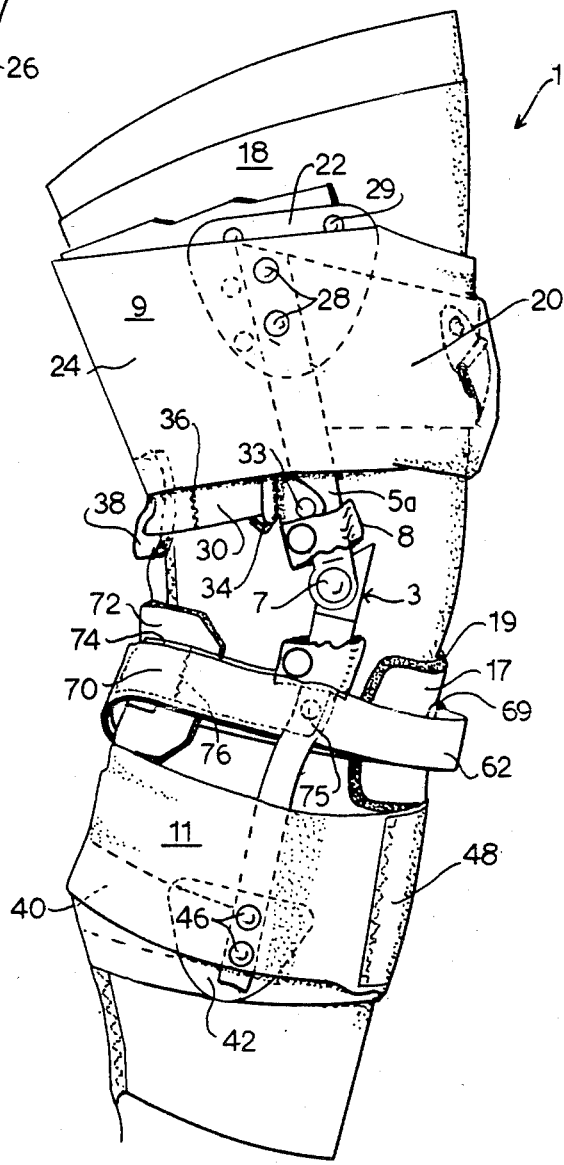
FIG. 2a
FIG. 2b

LIGHTWEIGHT, COMPACT ORTHOTIC DEVICE FOR CONTROLLING KNEE INSTABILITIES

BACKGROUND OF THE INVENTION

This invention generally relates to orthotic devices for controlling instabilities in joints, and is specifically concerned with an improved knee orthosis for correcting knee instabilities through a lightweight, compact mechanism which allows complete freedom of movement.

Orthotic devices for correcting knee instabilities are known in the prior art. Such devices are typically comprised of a mechanical joint that is supported by a pair of bracing members. The mechanical joint is formed from a pair of sidebars, each of which has a hinge-like pivoting joint in its middle portion. The top and bottom ends of the sidebars are connected to the bracing members. The bracing members fit around the regions of the leg above and below the kneejoint, and support the pivoting joints of the sidebars in alignment with the kneejoint so that the knee and the sidebars can pivot together as the wearer flexes his leg. Such prior art devices generally operate by confining the movement of the kneejoint as it bends so that unwanted motions of the lower femur and the upper tibia are eliminated or at least minimized.

Knee instabilities can take a variety of forms, including varus, valgus, rotary, anterior and posterior displacements, as well as hyperextension of the joint. Varus-type instabilities tend to bend the kneejoint outwardly, giving the leg a bow-legged orientation, while valgus instabilities tend to bend the kneejoint inwardly, giving the leg a knock-knee appearance. Rotary instabilities can cause the femural and tibial sections of the knee to rotate excessively with respect to one another as the knee flexes. Anterior instabilities tend to displace the tibia anteriorly with respect to the femur, while posterior instabilities tend to displace the tibia posteriorly as the knee flexes. Hyperextension-type instabilities allow the kneejoint to bend backward over 180°.

A properly installed orthotic knee brace can counteract all of these instabilities (at least in part) by reinforcing the kneejoint as a whole, and by supporting and guiding the lower femur and upper tibia as the kneejoint is flexed. Such devices are often needed by athletes competing in any running sport (such as football, hockey, tennis, etc.) who have suffered injuries to either the ligaments that interconnect the low er femur and upper tibia, or to the bones themselves, which make their joints much more prone to such unstable movements. For athletic applications, the ideal orthotic device would be capable of eliminating all such unstable movements through a mechanism that was extremely small and lightweight. Such a device would not diminish the speed or agility of the athlete to any significant extent, could be easily enclosed within a uniform, and would not rub against the other leg of the athlete when he was running.

Unfortunately, no such orthosis exists in the prior art that is capable of completely eliminating all such instabilities through a mechanical structure that is as lightweight and as compact as desired. The applicant believes that there are general reasons why the prior art has failed to develop an "ideal" knee orthosis. First, applicant is not aware of any prior art knee orthoses that are capable of applying a dynamic laterally directed stabilizing force to at least the inner condylar region as the knee flexes without impeding the motion of the knee. Hence, a "slack" exists in many prior art knee orthoses that allow s at least one of the previously discussed instabilities to occur to a significant degree. Secondly, the applicant has observed that not all of the aforementioned knee instabilities are equally common or equally debilitating, and that of all these instabilities, anterior tibial displacements are the most common and debilitating. Accordingly, control of anterior tibial displacements appears to be the key to controlling an unstable knee. Yet many prior art knee orthoses are not designed with any sort of priority in mind; instead, they allocate substantially the same amount of structure for each type of instability in an attempt to correct all instabilities simultaneously without regard for the fact that some types of instabilities are more common and debilitating than others. This lack of structural emphasis tends to make many prior art orthoses relatively heavy and bulky.

Clearly, there is a need for an improved knee orthosis that is capable of correcting all unwanted motions of an injured knee through a structure which concentrates on correcting the most common and debilitating knee instabilities in order to streamline the structure as much as possible. Ideally, such a mechanism should be simple, easy to construct and fit onto the knee of an athlete, and should resist slippage during vigorous athletic activity.

SUMMARY OF THE INVENTION

In its broadest sense, the invention is an orthotic device for controlling knee instabilities that comprises a joint structure, upper and lower support assemblies for supporting the joint structure over the knee joint, a condyle pad assembly having an upper portion disposed over at least one of the condyle regions of the knee, and mounting means for resiliently maintaining the upper portion of the condyle assembly in intimate supporting contact with the condyle region throughout the range of pivotal movement of the knee.

The condyle pad assembly may also include an anterior extension on its lower portion for intimately contacting and supprrting the upper section of the tibia against displacements. In the preferred embodiment, the condyle pad assembly is an L-shaped pad wherein the upper portion that contacts the condyle region and the lower portion that has the anterior extension are integrally connected.

The mounting means may include a resilient strap for applying a laterally directed lifting force on the upper portion of the condyle pad assembly throughout the entire range of pivotal movement of the knee. A Dring may be pivotally connected to the upper portion of the condyle pad assembly, and the middle portion of the resilient strap may loop through the D-ring, and its ends may be connected at different points to the upper support assembly so that the strap assumes a V-shaped configuration. Preferably, one of the end portions of the resilient strap is connected directly above the upper portion of the condyle pad assembly, while the other end is connected to the interior section of the support assembly, so that the middle portion of the strap simultaneously pulls the upper portion of the condyle pad assembly upwardly and laterally as the knee bends. Additionally, the elastic characteristics of the resilient strap may be selected so that the laterally directed, upward force that this strap applies to the condyle pad assembly stays the same or increases as the knee is bent without impeding the flexing of the knee.

Both the upper and the lower support assemblies may include a C-shaped band, one of which surrounds an anterior portion of the leg, and the other of which surrounds a posterior portion of the leg in an interlocking, forced coupling position. Such a configuration advantageously streamlines the orthosis by minimizing the amount of material in the upper and lower assemblies with little or no sacrifice to the support strength.

Finally, all of the interior, leg-contacting surfaces of the orthotic device are preferably covered with a layer of Neoprene® to prevent slippage. As a further precaution against slippage, an undersleeve is preferably slipped over the leg prior to the installation of the orthosis.

BRIEF DESCRIPTION OF THE SEVERAL FIGURES

FIG. 2A is an inner side view of the orthosis illustrated in FIG. 1A, illustrating how the condyle pad assembly covers the inner condyle region of the leg of the wearer, and FIG. 2B is an outer side view of the orthosis illustrated in FIG. 1A.

DETAILED DESCRIPTION OF THE PREFERRED EMBODIMENT

General Overview of the Structure and Operation of the Invention

Figure 1A:
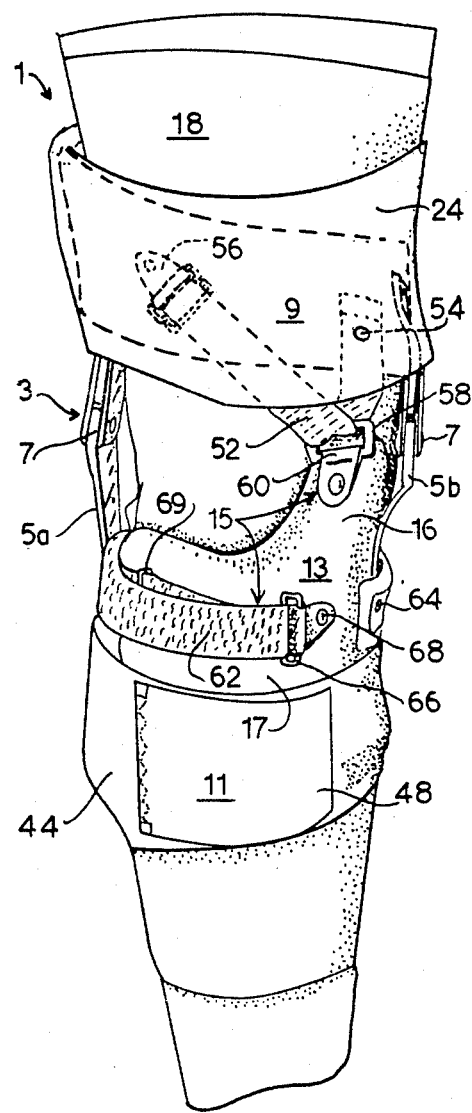
FIG. 1A is a front view of the orthotic device of the invention as it appears completely fitted onto the leg of a wearer.

With reference now to FIGS. 1A and 2B, the knee orthosis 1 of the invention includes a mechanical joint structure 3 formed from a pair of metallic sidebars 5a, 5b that are preferably made from either stainless steel or aluminum. Each of the sidebars 5a, 5b in turn includes a hinge structure 7 in its central portion that is alignable with the kneejoint of the wearer. As is best seen in FIG. 2B, each of the hinge structures 7 of the sidebars 5a, 5b is preferably constructed to resist being pivoted 170° in a manner which is well known in the art. The purpose of the 170° limit on the sidebars 5a, 5b is to prevent hyperextension of the kneejoint of the wearer. Finally, each of the hinge structures 7 of the sideaars 5a, 5b is preferably surrounded by a sleeve 8 formed from a resilient sheet material, such as foam Neoprene®. These sleeves 8 prevent the clothing of the wearer from becoming caught and bound within the moving components of the hinge structures 7 of the sidebars 5a, 5b.

Figure 1B:
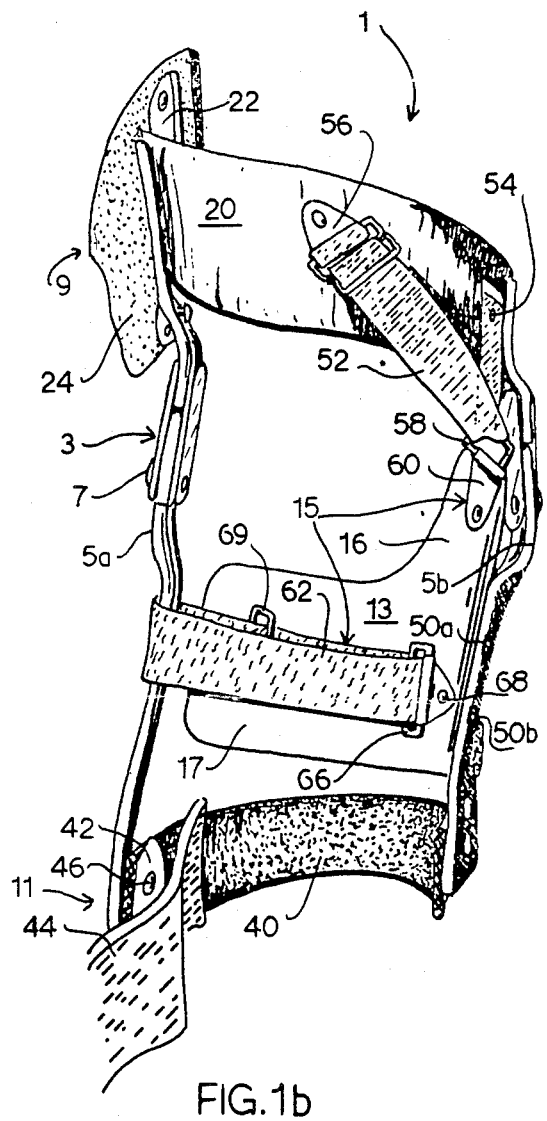
FIG. 1B is the orthosis illustrated in FIG. 1A as it appears without the leg of a wearer with the exterior foam Neoprene® straps rolled back.

With reference now to FIGS. 1A and 1B, upper and lower support assemblies 9, 11 surround the lower thigh and upper calf of the wearer and support the mechanical joint structure 3 into alignment with the knee. As will be described in detail hereinafter, a condyle pad assembly 13 is disposed between the upper and lower support assemblies 9 and 11 by a mounting means indicated generally at 15. The condyle pad assembly 13 is a generally L-shaped structure having an outer surface formed from flexible but relatively stiff sheet material such as Polyethylene. At its upper end, the condyle pad assembly 13 includes a condyle supporting portion 16 which engages the inner condyle region of the leg of the wearer when the orthosis is completely installed thereon. At its lower end, the condyle pad assembly 13 includes an anterior extension 17 which engages the upper tibia of the kneejoint of the wearer. The elasticity and specific V-shaped configuration of the straps forming the mounting means 15 maintain the upper end of the condyle supporting portion 16 of the assembly 13 in intimate supporting contact with the inner condylar region of the knee throughout the entire range of knee movement, while at the same time keeping the anterior extension 17 engaged against the tibia of the wearer, thereby preventing tibial displacement. The simultaneous support given to both the inner condylar region and the upper tibia of the kneejoint eliminates many of the most common knee instabilities with a structure which is minimal in size, weight and complexity. Finally, a stocking 18 slipped over the kneejoint of the wearer co-acts with a foam Neoprene® lining 19 adhered under the condyle pad assembly 13 in order to eliminate slippage between the pad assembly 13 and the kneejoint of the wearer.

SPECIFIC DESCRIPTION OF THE STRUCTURE AND OPERATION OF THE INVENTION

With reference now to FIGS. 1B, 2A and 2B, the upper support assembly 9 of the orthosis 1 includes a C-shaped band 20 formed from a material that is strong yet light, such as any one of a number of commercially available graphite composites. In the preferred embodiment, the interior of this C-shaped band 20 is molded to conform to the specific contours of the upper thigh of the wearer. The C-shaped band 20 is further slightly twisted with respect to the longitudinal axis of the leg so that its outer end is higher than its inner end when the upper support assembly 9 is installed. Such shaping of the C-shaped band 20 helps to prevent it from sliding downwardly toward the kneejoint of the wearer as a result of the downward and lateral forces applied to it by the V-shaped elastic strap of the mounting means 15.

As is best seen in FIG. 2B, a triangular lateral pad 22 is riveted to the inside of the outer end of the C-shaped band 20, while the upper end of the sidebar 5a is riveted to the outside of this area of the band 20. The end of a foam Neoprene® mounting strap 24 is further affixed to the inside surface of the triangular lateral pad 22. As may best be seen in FIG. 2A, the outer end of this strap 24 includes a Velcro® fastener 26 (best seen in FIG. 2A) that allows the strap 24 to be wound at least one and one-half times around the upper thigh of the wearer and then fastened upon itself. A pair of mounting rivets 28 extend through the outer end of the C-shaped band 20 to firmly sandwich the outer end of the C-shaped band 20 between the upper end of the sidebar 5a and the triangular lateral pad 22 on its inside, while other mounting rivets 29 are used to secure the fixed end of the strap 24 to the inner surface of the lateral pad 22. Other mounting rivets 29 secure the inner end of the strap 24 to the inner surface of the lateral pad 22 through a second Velcro® fastening device (not shown). This arrangement renders the inner end of the strap 24 detachably removable from the lateral pad 22 so that it may be easily replaced upon wearing out.

The last component of the upper support assembly 9 is a posterior mounting strap 30 best seen in FIGS. 2A and 2B. The inner end of the strap 30 is anchored to the outside of the inner sidebar 5b by means of a rivet 32. The outer end of the strap 32 loops around a D-ring 34 that is connected onto the outer sidebar 5a by means of another rivet 33. Like the previously described Neoprene ® strap 24, the posterior mounting strap 30 also includes a Velcro ® fastener 36 at its outer end. However, unlike the strap 24, the posterior mounting strap 30 is preferably formed from a relatively unresilient sheet material, such as nylon webbing. Finally, the posterior mounting strap 36 includes a pressure pad 38 for uniformly cistributing the pressure that the strap 30 applies to the posterior portion of the lower thigh when the orthosis 1 is installed. In operation, both the foam Neoprene ® strap 24 and the posterior mounting strap 30 co-act to maintain the C-shaped band 20 of the upper support assembly 9 firmly in place around the upper thigh of the wearer. By covering the various straps and buckles of the upper portion of the mounting means 15 of the condyle pad assembly 13, the foam strap 24 serves the additional function of providing a smooth exterior surface for the upper support assembly 9 that will not snag or bind on any clothing of the wearer of the orthosis 1.

As is best seen in FIGS. 1B, 2A and 2B, the lower support assembly 11 of the orthosis 1 of the invention also includes a C-shaped band 40. The outer end of the band 40 is connected to both a triangular lateral pad 42 and the lower end of the outer sidebar 5a. The inner end of another foam Neoprene ® strap 44 is connected to the inner surface of the triangular lateral pad 42 through another Velcro ® fastener (not shown). Mounting rivets 46 firmly sandwich the outer end of the C-shaped band 40 between the lower end of the sidebar 5a on its exterior and the triangular lateral pad 42 on its interior, while the inner end of the Neoprene ® strap 44 is detachably connected to the inner surface of the triangular lateral pad 42 by means of another Velcro ® fastener (not shown). Additionally, as is best seen in FIGS. 2A and 2B the outer end of the Neoprene strap 44 terminates in still another Velcro ® fastener 48 in order to render this end of the strap 44 detachably connectable to itself. Like strap 24, strap 44 is preferably capable of wrapping around the leg of the wearer about one and one-half times, and serves both to maintain the C-shaped band 40 around the leg of the wearer as well as to provide a smooth exterior surface for the lower support assembly 11.

With reference now to FIGS. 1A and 1B, the purpose of the mounting means 13 is to both mount the L-shaped condyle pad assembly 13 within the knee orthosis 1, as well as to maintain this pad in intimate supporting contact with both the inner condylar region of the knee and the upper tibia of the wearer. To this end, the mounting means 13 includes a pair of rivets 50a, 50b for connecting the inner edge of the lower portion of the L-shaped condyle pad assembly 13 to the inner sidebar 5b. In order to maintain the condyle supporting portion 16 of the pad 13 into supporting contact with the condylar region of the knee of the wearer, the mounting means 15 further includes a V-shaped elastic strap 52 that is connected to two points along the upper C-shaped band 20 by rivet 54 and pivoting buckle 56, respectively. The midportion of this V-shaped elastic strap 52 extends through the D ring 58 of a pivoting buckle 60 connected to the upper end of the pad 13. In operation, the elastic strap 52 applies an inwardly and upwardly directed force to the condyle supporting portion 16 of the pad 13 in order to maintain it firmly against the inner condylar region of the knee. The sliding engagement between the D ring 58 and the central portion of the strap 52 maintains this inwardly and upwardly directed supporting force at approximately the same angle with respect to theinner condylar region of the knee despite the pivoting motion between the strap and the pad assembly 13 caused by the flexing of the knee of the wearer. In the preferred embodiment, the elastic properties of the V-shaped strap 52 are chosen so that the magnitude (as opposed to the angle) of the inwardly and upwardly directed force applied to the condyle supporting portion 16 either stays the same or increases as the knee is bent.

Finally, with reference again to FIGS. 1B, 2A and 2B, the mounting means 15 of the orthosis 1 also includes a strap 62 for maintaining the anterior extension of the condyle pad assembly 13 into intimate supporting engagement with the tibia of the wearer. One end of the strap 62 is anchored to the inner sidebar 5b of the orthosis 1 by means of rivet 64, while the other end of the strap 62 is threaded through the D ring 66 of a pivoting buckle 67 mounted onto the lower end of the pad assembly 13. A guide ring 69 is further provided on the lower end of the pad assembly 13 for maintaining the alignment of the strap 62. The outer end of the strap 62 includes a Velcro ® fastener 70 which allows the strap 62 to be detachably connected to either itself or another Velcro ® fastener at its posterior portion. A pressure pad 72 is included on the posterior strap 62 for the same reasons given with respect to the pressure pad 38. In order to prevent the sidebar 5a from moving with respect to the strap 62, a lateral support strap 74 (shown in FIG. 2B) is connected to the sidebar 5a by a rivet 75. This relatively short strap 74 is sandwiched between the overlapping portions of the strap 62, and includes a Velcro ® fastenr 76 on both of its sides to allow it to securely fasten itself between the overlapping portions of strap 62.

In operation, the combination of the V-shaped elastic strap 52 and the strap 62 of the mounting means 15 dynamically the condyle supporting portion 16 and the anterior extension 17 of the L-shaped condyle pad assembly 13 into intimate supporting contact against the inner condylar region and the upper tibia of the knee, respectively, thereby firmly supporting the knee against anterior tibial displacements. The specific mounting configuration of the V-shaped strap 52 and its specific eleastic properties result in a support force whose direction does not change, and whose magnitude either stays the same or increases slightly as the knee is bent. Additionally, the combination of the support given to the knee as a whole by the condyle supporting portion 16, the sidebars 5a, 5b and the upper and lower support assemblies 9, 11 of the orthosis protect the leg from varus, valgus, and rotary instabilities, as well as hyperextension. Finally, the foam Neoprene ® lining 19 of the pad assembly 19, in combination with the foam Neoprene ® straps 24, 44 and stocking 18 of the wearer help to prevent the orthosis from slipping out of position on the wearer's leg during vigorous physical activity.

We claim:
1. An orthotic device for controlling knee instabilities, comprising:
 a. a joint structure;
 b. an upper support assembly including side portions and an anterior portion, and a lower support assembly for circumscribing the leg above and below the kneejoint and connected to the joint structure for supporting the joint structure over the kneejoint;

c. a condyle pad assembly having an upper portion for engaging one of the condyle regions of the kneejoint; and d. mounting means including a resilient strap for applying a lifting force on the upper portion of the condyle pad assembly and a D-ring means connected to the upper portion of the condyle pad assembly, wherein one end of the resilient strap is connected to the side portion of the upper support assembly that lies above the condyle region of the kneejoint, the other end of the resilient strap is connected to the anterior portion of the upper support assembly, while a middle portion of the resilient strap pulls the upper portion of the condyle pad assembly both upwardly and laterally to resiliently maintain the upper portion of the condyle pad assembly in intimate supporting contact with the condyle region throughout the range of pivotal movement of the kneejoint.

2. The device of claim 1, wherein said condyle pad assembly includes an anterior extension of its lower portion for supporting the upper section of the tibia against displacements.

3. The device of claim 2, wherein said mounting means further includes a strap means for engaging said anterior extension into intimate supporting contact with the upper section of the tibia.

4. The device of claim 1, wherein the mounting means includes adjustment means for adjusting the amount of laterally directed lifting force that the resilient strap applies to the upper portion of the 5. The device of claim 1, wherein the upper support assembly includes a C-shaped band for surrounding the sides and anterior portion of the lower thigh, and a strap means for securing the band around the lower thigh of the wearer.

6. The device of claim 5, whereint he lower support assembly also includes a C-shaped band for surrounding the sides and posterior portion of the upper calf, and a strap means for securing this band around the upper calf of the wearer.

7. The device of claim 1, wherein the knee-contacting side of the condyle pad assembly includes a layer of an anti-slippage sheet material.

8. An orthotic device for controllng knee instabilities, comprising:

a. a joint structure;

b. an upper support assembly including side portions and an anterior portion, and a lower support assembly for circumscribing the leg above and below the kneejoint and connected to the joint structure for supporting the joint structure over the kneejoint;

c. a substantially L-shaped condyle pad assembly having an upper portion for supporting an inner condyle region of the kneejoint, and an anterior extension on a lower portion for supporting an upper section of the tibia against anterior displacements; and d. mounting means including a resilient strap for applying a lifting force on the upper portion of the condyle pad assembly and a D-ring means connected to the upper portion of th e condyle pad assembly, wherein one end of the resilient strap is connected to the side portion of the upper support assembly that lies above the condyle region of the kneejoint, the other end of the resilient strap is connected to the anterior portion of the upper support assembly, while a middle portion of the resilient strap pulls the upper portion of the condyle pad assembly both upwardly and laterally to resiliently maintain the upper portion of the condyle pad assembly in intimate supporting contact with the condyle region throughout the range of pivotal movement of the kneejoint.

9. The device of claim 13, wherein the resilient characteristics of said strap are such that the laterally directed lifting force applied onto the upper portion of the condyle pad assembly increases as the kneejoint is bent.

10. The device of claim 9, wherein the D-ring of the mounting means is pivotally connected to the upper portion of the condyle pad assembly.

11. The device of claim 8, wherein each of the upper and lower support assemblies includes a C-shaped band, one for surrounding an anterior portion of the leg, the other for surrounding the posterior portion of the leg.

12. The device of claim 8, wherein the interior, leg-contacting surfaces of the orthotic device are substantially covered by a layer of Neoprene ® to prevent slippage.

13. The device of claim 8, wherein the mounting means includes adjustment means for adjusting the amount of laterally directed lifting force that the resilient strap applies to the upper portion of the condyle pad assembly.

14. An orthotic device for attachment to the leg of a user for controlling knee instabilities while permitting operation of the kneejoint, comprising:

a. an upper support assembly means for circumscribing the leg above the knee and including side portions and an anterior portion;

b. a lower support assembly means for circumscribing the leg below the knee;

c. a joint structure secured to and extending between said upper and lower support assembly means, said upper and lower support assembly means operating to support said joint structure in alignment with said kneejoint;

d. a condyle pad assembly having an upper condyle supporting portion and a lower portion integrally formed with said upper portion, said lower portion including an anterior extension, e. and mounting means for mounting said condyle pad assembly between said upper and lower support assembly means with said condyle supporting portion in engagement with the inner condyle region of the leg and the anterior extension in engagement with the upper tibia of the kneejoint, said mounting means including strap support means mounted upon said upper condyle supporting portion, a first resilient strap means having a first end connected to a side portion of said upper support assembly means at a point above the condyle region of the kneejoint, a second end connected to the anterior portion of the upper support assembly means, and a middle portion between said first and second ends being retained by said mounting means to form a "V" configuration of said first resilient strap means to cause the first resilient strap means to apply a lifting force to the upper condyle supporting portion and pull the upper condyle supporting portion upwardly and laterally to resiliently maintain the upper condyle supporting portion in intimate contact with the condyle region throuogut the range of pivotal movement of the kneejoint, and second resilient strap means connected between said joint structure and said lower portion of said condyle pad assembly for maintaining said anterior extension in intimate supporting engagement with the tibia.

* * * * *